US008532783B2

(12) United States Patent
Zimmerling et al.

(10) Patent No.: US 8,532,783 B2
(45) Date of Patent: Sep. 10, 2013

(54) IMPACT PROTECTION FOR IMPLANTS

(75) Inventors: Martin Zimmerling, Patsch (AT); Gerhard Mark, Axams (AT); Dominik Hammerer, Innsbruck (AT)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 292 days.

(21) Appl. No.: 13/105,565

(22) Filed: May 11, 2011

(65) Prior Publication Data

US 2011/0270370 A1 Nov. 3, 2011

Related U.S. Application Data

(63) Continuation-in-part of application No. 12/207,715, filed on Sep. 10, 2008, now abandoned.

(60) Provisional application No. 60/971,021, filed on Sep. 10, 2007.

(51) Int. Cl.
*A61N 1/372* (2006.01)

(52) U.S. Cl.
USPC .......................................................... 607/57

(58) Field of Classification Search
USPC .......................................................... 607/57
See application file for complete search history.

(56) References Cited

U.S. PATENT DOCUMENTS

| 4,014,346 | A | 3/1977 | Brownlee et al. | 128/419 PS |
| 5,330,826 | A | 7/1994 | Taylor et al. | 428/216 |
| 5,477,855 | A | 12/1995 | Schindler et al. | 128/642 |
| 6,011,993 | A | 1/2000 | Tziviskos et al. | 607/36 |
| 7,346,391 | B1 | 3/2008 | Osorio et al. | 607/2 |
| 2002/0019669 | A1 | 2/2002 | Berrang et al. | 623/10 |
| 2003/0109903 | A1 | 6/2003 | Berrang et al. | 607/36 |
| 2006/0116743 | A1 | 6/2006 | Gibson et al. | 607/57 |
| 2006/0200200 | A1 | 9/2006 | Malinowski et al. | 607/2 |
| 2009/0069892 | A1 | 3/2009 | Zimmerling et al. | 623/11.11 |

FOREIGN PATENT DOCUMENTS

WO WO 2004/014270 A1 2/2004

OTHER PUBLICATIONS

"DIN EN 45502-2-3; 0750-10-3; Feb. 2007 Aktive implantierbare Medizingerate 0 Teil 2-3: Bosondere Festegungen fur Cochlear-Implante; Deutsche Fassung prEN 4550-2-3:2006" Feb. 28, 2007. BDE VERLAG, Berling, XP009110711, second half including English language translation of German text.
International Searching Authority, International Search Report and Written Opinion dated Jan. 26, 2009, 5 pages, application No. PCT/US2008/075777.
United States Patent and Trademark Office, Office Action dated Sep. 21, 2009, 21 pages, U.S. Appl. No. 12/207,715.
International Searching Authority, International Preliminary Report on Patentability, dated Mar. 25, 2010, 7.2 pages, application No. PCT/US2008/075777.

(Continued)

*Primary Examiner* — Carl H Layno
*Assistant Examiner* — Luther Behringer
(74) *Attorney, Agent, or Firm* — Sunstein Kann Murphy & Timbers LLP

(57) ABSTRACT

An implantable device includes an implantable housing having an outer surface and providing a hermetically sealed interior volume. A flexible electric lead is mechanically connected to the housing and electrically connected to circuitry within the interior volume. An impact protector overlies at least a portion of the outer surface of the housing and shields the underlying housing surface from the force of a mechanical impact. At least a portion of the impact protector may include an electrode electrically connected to the circuitry within the interior volume.

19 Claims, 2 Drawing Sheets

(56) References Cited

OTHER PUBLICATIONS

United States Patent and Trademark Office, Office Action dated Sep. 15, 2010, 15 pages, U.S. Appl. No. 12/207,715.
United States Patent and Trademark Office, Office Action dated Feb. 11, 2011, 7 pages, U.S. Appl. No. 12/207,715.
Australian Patent Office, Examination Report dated Mar. 31, 2011, 3 pages, application No. 2008299049.
United States Patent and Trademark Office, Office Action dated Apr. 15, 2010, 11 pages, U.S. Appl. No. 12/207,715.
T. Sekino et al., "Percolation Analysis of Electrical Conductivity and Mechanical Properties for CNT-dispersed Y-TZP Nanocomposites" Advances in Technology vol. 45, Oct. 10, 2006, pp. 1469-1474.

(A)

(B)

(C)

(D)

(A)

(B)

(C)

(D)

(E)

IMPACT PROTECTION FOR IMPLANTS

CROSS REFERENCE TO RELATED APPLICATIONS

This application is a continuation-in-part of U.S. patent application Ser. No. 12/207,715, filed Sep. 10, 2008, now abandoned, titled "Impact Protection for Implants," the entire contents of which are hereby incorporated by reference herein. Through U.S. patent application Ser. No. 12/207,715, this application claims the benefit of U.S. Provisional Patent Application No. 60/971,021, filed Sep. 10, 2007, titled "Impact Protection for Implants," the entire contents of which are hereby incorporated by reference herein.

TECHNICAL FIELD

The present invention relates to medical devices, and specifically, to implantable medical devices.

BACKGROUND ART

Implantable medical devices such as cochlear implants can be subject to occasional or regular mechanical impact. It is important that implantable devices be able to sustain such impacts and continue normal functioning. The proposed European standard EN 45502-2-3 for cochlear implants mandates an impact robustness standard for an impact energy which initially will be 1.5 Joules, which increases three years later to 2.5 Joules.

SUMMARY OF EMBODIMENTS

Embodiments of the present invention are directed to a device that is implantable in a body. At least one implantable housing with an outer surface provides a hermetically sealed interior volume. A flexible electric lead is mechanically connected to the housing and electrically connected to circuitry within the interior volume. An impact protector, distinct from the at least a portion of the outer surface of the housing, overlies the at least a portion of the outer surface of the housing. The impact protector is configured to distribute at least a portion of force resulting from a mechanical impact over at least the portion of the housing and transfer at least a portion of the force, through the housing, to the body, without a rigid anchoring structure connected to the body. At least a portion of the impact protector includes an electrode electrically connected to the circuitry within the interior volume.

In further specific embodiments, the impact protector further overlies and shields at least a portion of the electric lead. The electric lead further connects to multiple implantable stimulation electrodes, for example, as in a cochlear implant, an auditory brainstem implant or a middle-ear implant. The impact protector may shield at least a portion of the outer surface from impacts of defined energy, such as at least 1.5 J or 2.5 J.

The impact protector may be a metallic sheet manufactured from high-strength metal or alloy like steel or platinum-iridium. Or, the impact protector can be made of ceramic material such as zirconium oxide, yttrium-stabilized zirconia, alumina, or zirconium toughened alumina. Or the impact protector may be made of fiber-reinforced materials such as carbon or carbon fiber. The impact protector may be combination of the above materials such as a composite structure consisting of a first layer of ceramic material and a second layer of a sheet metal or other combinations. The impact protector may include a composite material that includes two or more of the following: sheet metal, sheet metal including platinum-iridium, ceramic, zirconium oxide, yttrium-stabilized zirconia, alumina, zirconium-toughened alumina, a fiber-reinforced material and carbon fiber. The impact protector may include a ceramic material, and the electrode may include an electrode contact attached to the ceramic material. In some embodiments, the impact protector has a cambered surface.

In some embodiments, the at least one implantable housing may include multiple implantable housings. In specific such embodiments, the impact protector may overlay potions of multiple housings or just one of the housings.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Figure 1:
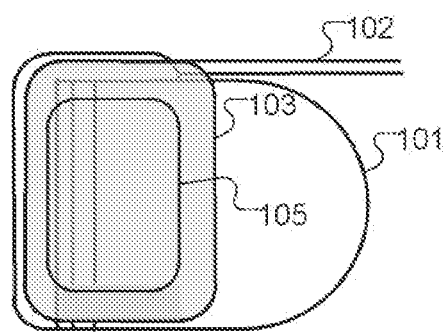
FIG. 1A-D shows top plan views of various specific embodiments of impact protectors for an implantable device.
Figure 1:
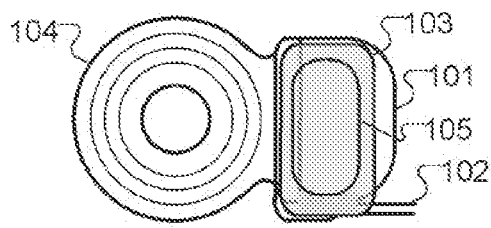
Figure 1:
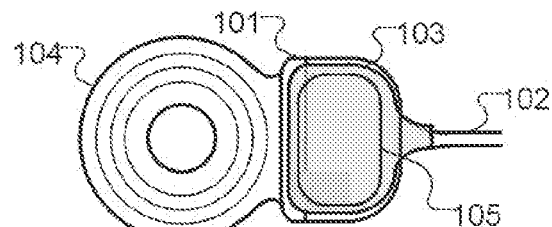
Figure 1:
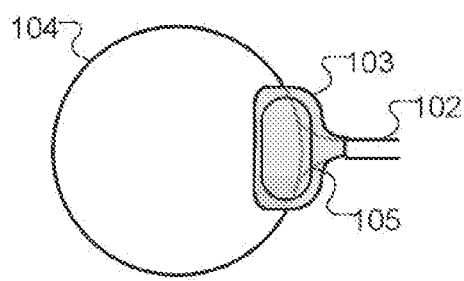

Various embodiments of the present invention are directed to providing impact protection for implantable devices; for example, a cochlear implant system may be implanted in a human body. FIG. 1A-D shows top plan views of various specific embodiments of impact protectors for an implantable device, and FIG. 2A-E shows side views of various specific embodiments of impact protectors. At least one implant housing 101 provides a hermetically sealed interior volume containing various functional elements, such as circuitry, of an implant system. In specific embodiments, the implant housing 101 is typically made of a strong bio-compatible material such as ceramic, pure metal or metal alloys. In some embodiments, there may be only a single implantable housing 101, while in others, there may be multiple such housings, which are interconnected.

A flexible electric lead 102 is mechanically connected to the implant housing 101 and also electrically connected to the functional elements within the interior volume. In the specific case where the implantable device is a cochlear implant, the electric lead 102 may connect with or be a part of the electrode stimulator that is inserted in the patient cochlea. In some embodiments, impact resistance may also be improved by controlling the angle at which the electrode lead 102 connects to the side of the implant housing 101 such that the electrode lead is away from the lateral side of the housing which is most susceptible to impact.

An impact protector 103 overlies at least a portion of the outer surface of the implant housing 101 and shields the underlying housing surface from the force of a mechanical impact. The impact protector is distinct from the at least the portion of the outer surface of the housing. The impact protector 103 absorbs some significant amount of the force from mechanical impacts to the device, which in the prior art had to be completely absorbed by the implant housing 101. In some specific embodiments, the impact protector 103 may not only absorb impact energy, but also may deflect the impact energy to parts of the implant housing 101. The impact protector 103 is configured to distribute at least a portion of force resulting from a mechanical impact over at least the portion of the housing 101 and transfer at least a portion of the force, through the housing 101, to the body, without a rigid anchoring structure connected to the body. The impact protector 103 does not, for example, include "ears," by which the impact protector 103 may be attached to bone. At least a portion of the impact protector 103 may include an electrode 105 electrically connected to the circuitry within the interior volume. In specific embodiments in which there are multiple implantable housings 101, the impact protector 103 may overlay portions of multiple housings or just one of the housings.

FIG. 1A-D and FIG. 2B-C show specific embodiments in which the impact protector 103 covers portions of the implant housing 101 and further overlies and shields at least a portion of the electric lead 102. In some specific embodiments, the impact protector 103 on top of the implant housing 101 can be extended to the side of the implant housing 101 or parts of it (e.g. electrode lead 102) in order to achieve impact protection also from the side.

Figure 2:
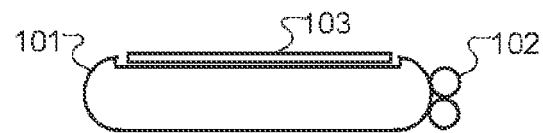
FIG. 2A-E shows side views of various specific embodiments of impact protectors for an implantable device.
Figure 2:
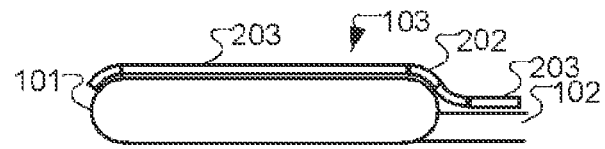
Figure 2:
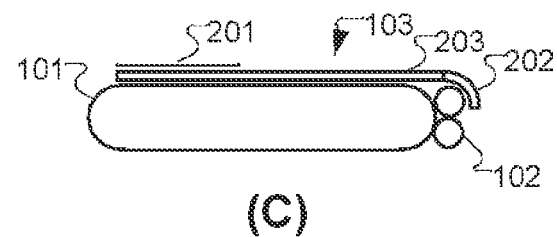
Figure 2:
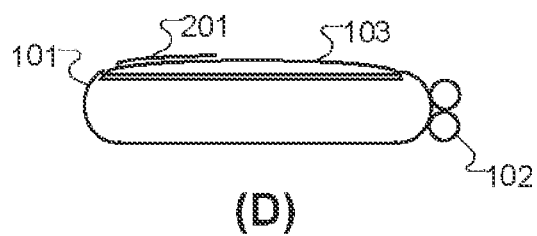
Figure 2:
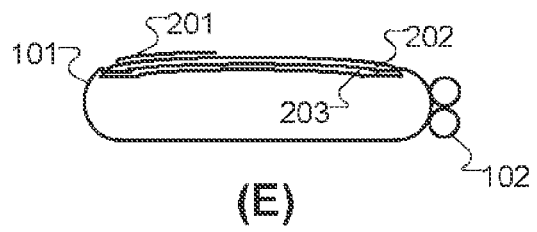

The impact protector 103 may be in the specific form of a sheet metal such as a steel or platinum-iridium sheet. Such an embodiment may be mounted as shown in FIG. 2A on a lateral side of the implant housing 101, which increases impact robustness at that lateral side. As a result, the walls of the implant housing 101 enclosing the hermetically sealed interior volume may be thinner and the design can have reduced headroom and a thinner overall device design.

In other specific embodiments, the impact protector 103 may be made of ceramic material, preferably with a high fracture toughness, such as zirconium oxide, YTZP (yttrium-stabilized zirconia), ZTA (zirconium toughened alumina), and oxide- and non-oxide ceramic materials of high impact-resistance. Compared to a metallic impact protector 103, a ceramic one may have a higher initial and total accumulative impact robustness for the same overall thickness of material and/or may allow a thinner design for the same impact robustness.

Compared to a metal impact protector 103, a ceramic one has other advantages. A metallic impact protector 103 deforms somewhat in response to a mechanical impact, which requires some headroom be provided as a safety margin to protect the components within the interior volume of the implant housing 101, but a ceramic one will not exhibit plastic deformation on impact and thus the overall thickness of the device can be further reduced. A ceramic impact protector 103 is electrically isolating, and in some embodiments, as shown for example in FIG. 2C-2E, an electrode contact 201 may be mounted onto the ceramic impact protector 103.

A ceramic impact protector 103 may also be more compatible with post-surgical medical procedures. For example, a ceramic impact protector 103 may be better suited than a metallic one for MRI imaging in that the (susceptibility) artifact of a ceramic impact protector is smaller than that of a metallic one. Also, a ceramic impact protector 103 (with or without a thin foil electrode attached) has a reduced overall metal volume and reduced thermal capacity, so that any potential heating effects during magnetic resonance imaging (MRI) are reduced. In addition, a ceramic impact protector 103 generates a smaller dose of secondary electrons during exposure to ionizing irradiation (as is used for therapeutic irradiation). Thus the risk of necrosis around the implanted device due to a local overdose of ionizing irradiation is reduced. A ceramic impact protector 103 also has reduced opacity as compared to a relatively massive metal impact protector which may be advantageous, e.g., if the implanted device uses optical data transmission or if the implant status or identification needs to be checked by x-ray or CT scan.

Alternatively, the impact protector 103 could be made of some other relatively strong bio-compatible material such as carbon, carbon fiber, or fiber-reinforced compound material. A protector made of ceramics (ceramic pad) or carbon (or carbon fibers) instead of the metal or alloy sheet (such as steel or Platinum Iridium alloy or other high strength alloy formulation) or together with a thinner and/or smaller metal or alloy sheet could be used to protect the stimulator part of the implant as well as the electrode lead (which may exit the stimulator housing either in tangential or radial direction). The impact protector 103 does not necessarily need to be hermetic as long as it is not part of the hermetic encapsulation of the implant.

In some embodiments, impact protector 103 may include both metallic and ceramic material. For example, as shown in FIG. 2B, impact protector 103 may include flat ceramic material 203 and cambered metallic material 202. In other embodiments, the metallic material 202 may be flat and the ceramic material 203 may be cambered. FIG. 2C shows an embodiment having a flat ceramic region 203 over the implant housing 101 and a cambered metallic portion 202 over and protecting the implant lead 102. FIG. 2E shows an embodiment having a first layer of ceramic material 203 and a second layer of a metallic material 202, both layers being cambered. In a specific embodiment as shown in FIG. 2E, the layer of ceramic material 203 might be 0.25 mm thick, and the metallic material 202 might be a platinum layer 0.025 mm thick attached by some adhesive such as silicone adhesive. In some embodiments, impact protector 103 may be of varying thickness. The impact protector 103 may include a composite material that includes two or more of the following: sheet metal, sheet metal including platinum-iridium, ceramic, zirconium oxide, yttrium-stabilized zirconia, alumina, zirconium-toughened alumina, a fiber-reinforced material and carbon fiber.

In various embodiments, impact resistance may also be improved by optimizing the geometry of the implant housing 101, e.g., by increasing the wall thickness and/or by using a more impact-resistant ceramic material in the body of the housing. In some embodiments, the implant housing 101 may be made of or encapsulated with titanium to increase the impact robustness of the implanted device. For example, implant housing 101 may include double housing shell of deep-drawn or machined titanium with at least one of the shells acting as hermetic encapsulation.

Although various exemplary embodiments of the invention have been disclosed, it should be apparent to those skilled in the art that various changes and modifications can be made which will achieve some of the advantages of the invention without departing from the true scope of the invention.

What is claimed is:

1. A device implantable in a body, the device comprising:
   at least one implantable housing having an outer surface and providing a hermetically sealed interior volume;
   a flexible electric lead mechanically connected to the housing and electrically connected to circuitry within the interior volume; and
   an impact protector overlying, and distinct from, at least a portion of the outer surface of the housing and configured to distribute at least a portion of force resulting from a mechanical impact over at least the portion of the housing and transfer at least a portion of the force, through the housing, to the body, without a rigid anchoring structure connected to the body, at least a portion of the impact protector comprising an electrode electrically connected to the circuitry within the interior volume.

2. An implantable device according to claim 1, wherein the impact protector further overlies and shields at least a portion of the electric lead.

3. An implantable device according to claim 1, wherein the electric lead further connects to a plurality of implantable stimulation electrodes.

4. An implantable device according to claim 1, wherein the device is one of a cochlear implant, an auditory brainstem implant, and a middle-ear implant.

5. An implantable device according to claim 1, wherein the impact protector shields the at least a portion of the outer surface from forces resulting from an impact having an energy of at least 1.5 J.

6. An implantable device according to claim 5, wherein the impact protector shields the at least a portion of the outer surface from forces resulting from an impact having an energy of at least 2.5 J.

7. An implantable device according to claim 1, wherein the impact protector is a sheet metal.

8. An implantable device according to claim 7, wherein the sheet metal is made of platinum-iridium.

9. An implantable device according to claim 1, wherein the impact protector is made of ceramic material.

10. An implantable device according to claim 9, wherein the ceramic material is zirconium oxide, yttrium-stabilized zirconia, alumina or zirconium toughened alumina.

11. An implantable device according to claim 1, wherein the impact protector is made of fiber-reinforced material.

12. An implantable device according to claim 11, wherein the fiber-reinforced material is a carbon fiber.

13. An implantable device according to claim 1, wherein the impact protector includes a first layer of ceramic material and a second layer of sheet metal.

14. An implantable device according to claim 1, wherein the impact protector comprises a composite material comprising a plurality of materials selected from: sheet metal, sheet metal including platinum-iridium, ceramic, zirconium oxide, yttrium-stabilized zirconia, alumina, zirconium-toughened alumina, a fiber-reinforced material and carbon fiber.

15. An implantable device according to claim 1, wherein the impact protector has a cambered surface.

16. An implantable device according to claim 1, wherein the at least one implantable housing includes a plurality of interconnected implantable housings.

17. An implantable device according to claim 16, wherein the impact protector overlays a portion of one of the housings.

18. An implantable device according to claim 16, wherein the impact protector overlays a portion of a plurality of the housings.

19. An implantable device according to claim 1, wherein the impact protector comprises a ceramic material and the electrode comprises an electrode contact attached to the ceramic material.

* * * * *